United States Patent
Bloodworth

(10) Patent No.: US 9,706,726 B2
(45) Date of Patent: *Jul. 18, 2017

(54) **SSC INDUCTION IN *VITIS MUSCADINIA***

(71) Applicant: SCARLET TANAGER LLC, Lawrenceburg, IN (US)

(72) Inventor: Patterson Jeffrey Bloodworth, Hillsborough, NC (US)

(73) Assignee: SCARLET TANAGER LLC, Lawrenceburg, IN (US)

( * ) Notice: Subject to any disclaimer, the term of this patent is extended or adjusted under 35 U.S.C. 154(b) by 423 days.

This patent is subject to a terminal disclaimer.

(21) Appl. No.: 14/205,925

(22) Filed: Mar. 12, 2014

(65) Prior Publication Data

US 2014/0283164 A1    Sep. 18, 2014

Related U.S. Application Data

(60) Provisional application No. 61/790,703, filed on Mar. 15, 2013.

(51) Int. Cl.
*A01H 5/08* (2006.01)
*A01H 1/02* (2006.01)

(52) U.S. Cl.
CPC ............................ *A01H 5/0812* (2013.01)

(58) Field of Classification Search
None
See application file for complete search history.

(56) References Cited

U.S. PATENT DOCUMENTS 9,045,767 B2 *   6/2015   Bloodworth .......   C12N 15/8286

OTHER PUBLICATIONS

Ramming et al. (Hortscience 35(4):732-734. 2000).*
U.S. Appl. No. 14/061,322, filed Oct. 23, 2013, Scarlet Tanager.
Alston, et al. 1997. The California Table Grape Commission's Promotion Program: An Evaluation. Giannini Foundation Monograph No. 43. 122 p.
Bouquet, A. and M. Hevin. 1978. Green-grafting between Muscadine grape (Vitis rotundifolia Michx.) and bunch grapes (Euvitis sppl) as a tool for physiological and pathological investigations. Vitis 17:134-138.
Cain, et al., 1983. In-ovulo embryo culture and seedling development of seeded and seedless grapes (*Vitis vinifera* L.). Vitis 22:9-14.
Dearing, C. 1917. Muscadine Grape Breeding. J. Hered. 8:409-424.
Detjen, L. R. 1919a. The limits in hybridization of *Vitis rotundifolia* with related species and genera. N.C. Agr. Expt. Sta. Tech. Bul. 17.
Detjen, L. R. 1919b. Some $F_1$ Hybrids of *Vitis rotundifolia* with related species and genera. N.C. Agr. Expt. Sta. Tech. Bul. 18.
Dunstan, R. T. 1962. Some fertile hybrids of bunch and muscadine grapes. J. Hered. 53:299-303 (Corrigendum, 1963. 54:25).
Dunstan, R. T. 1964. Hybridization of *Euvitis* x *Vitis rotundifolia*: backcrosses to muscadine. Proc. Am. Soc. Hort. Sci. 84:238-242.
Emershad, R. L. And D. W. Ramming. 1984. In-ovulo embryo culture of *Vitis vinifera* L. C.V. 'Thompson Seedless'. Am. J. Bot. 71:873-877.
Fry, B. O. 1964. Fertile interspecific hybrids *Vitis rotundifolia* x *Vitis vinifera*. Ga. Agr. Expt. Sta. Mimeo. Series N.S. 200.
Goldy, et al. 1988. Embryo culture as a means of introgressing seedlessness from *Vitis vinifera* to *V. rotundifolia*. HortScience 23:886-889.
Goldy, R. G. 1992. Breeding Muscadine Grapes. Horticultural Reviews 14:357-405.
Jelenkovic, G., and H. P. Olmo. 1968. Cytogenetics of *Vitis* III. Partially fertile $F_1$ diploid hybrids between *V. vinifera* x *V. rotundifolia* Michx. Vitis 7:281-293.
Jelenkovic, G., and H. P. Olmo. 1969. Cytogenetics of *Vitis* IV. Backcross derivatives of *V. vinifera* x *V. rotundifolia* Michx. Vitis 8:1-11.
Ledbetter, C. A. and D. W. Ramming. 1989. Seedlessness in Grapes. Horticultural Reviews 11:159-184.
Lu, et al. 1993. Introgression of seedlessness from bunch grapes into muscadine grapes. Proc. Fla. State Hort. Soc. 106:122-124.
Lu, J. and O. Lamikanra. 1996. Barriers to intersubgeneric crosses between *Muscadinia* and *Euvitis*. HortScience 31:269-271.
Lu, J. 2001. The Grape Genetics, Breeding and Viticulture Program, Center for Viticultural Sciences, Florida A&M University. Report to SERA-IEG14 Group. 10 p.
Merdinoglu, et al. 2002. Genetic Analysis of Downy Mildew Resistance derived from *Muscadinia rotundifolia*. ISHS Acta Horticulturae 603: VIII International Symposium on Grape Genetics and Breeding.
Olmo, H. P. 1971. Vinifera rotundifolia hybrids as wine grapes. Am. J. Enol. Vitic. 22:87-91.
Patel, G. I. and H. P. Olmo. 1955. Cytogenetics of *Vitis:* I. The hybrid *V. vinifera* x *V. rotundifolia*. Amer. J. Bot. 42:141-159.
Qu, et al. 1996. Genetic diversity in Muscadine and American bunch grapes based on randomly amplified polymorphic DNA (RAPD) analysis. J. Amer. Soc. Hort. Sci. 121(6):1020-1023.
Ramming, et al. 2000. A stenospermocarpic, seedless *Vitis vinifera* x *Vitis rotundifolia* hybrid developed by embryo rescue. HortScience 35:732-734.
Ramming, et al. 2012. Identification of Race-Specific Resistance in North American *Vitis* spp. Limiting *Erysiphe necator* Hyphal Growth. Phytopathology 102:83-93.
Riaz, et al. 2011. Using a limited mapping strategy to identify major QTLs for resistance to grapevine powdery mildew (*Erysiphe necator*) and their use in marker-assisted breeding. Theor. Appl. Genet. 122:1059-1073.

(Continued)

*Primary Examiner* — Elizabeth McElwain
*Assistant Examiner* — Charles Logsdon
(74) *Attorney, Agent, or Firm* — Jondle & Associates, P.C.

(57) ABSTRACT

This invention relates to a method for introgressing a form of seedlessness, viz. stenospermocarpy (SSC) from subgenus *Euvitis* Planch. across a partial sterility barrier and partial pollen incompatibility barrier into subgenus *Muscadinia* Planch. and the plants produced by the method.

15 Claims, No Drawings

(56) References Cited

OTHER PUBLICATIONS

Spiegel-Roy, et al. 1985. In vitro culture and plant formation from grape cultivars with abortive ovules and seeds. J. Am. Soc. Hort. Sci. 110:109-112.

Bilderback, et. al., Grafting and Budding Nursery Crop Plants, Jun. 30, 2014, NC State University, http://content.ces.ncsu.edu/grafting-and-budding-nursery-crop-plants.

Bouquet, A., Differences observed in the graft compatibility between some cultivars of Muscadine grape (Mitis rotundifolia Michx.) and European grape (Mitis vinifera L. cv. Cabernet Sauvignon), Vitis, 1980, 19: 99-104.

Mudge, et. al., A History of Grafting, Horticultural Reviews, 2009, vol. 35: Chapter 9: 437-493, John Whey & Sons, Inc.

Ren, Z. and J. Lu, Muscadine rootstock increased the resistance of Florida hybrid bunch grape cv. 'Blanc du Bois' to Pierce's and anthcranose diseases, Proc. Fla. State Hort. Soc., 2002, 115: 108-110.

\* cited by examiner

SSC INDUCTION IN *VITIS MUSCADINIA*

CROSS REFERENCE TO RELATED APPLICATIONS

This application claims the benefit of priority from U.S. provisional patent application Ser. No. 61/790,703 filed on Mar. 15, 2013, which is incorporated herein by reference in its entirety.

BACKGROUND OF THE INVENTION

This present invention relates to a method for introgressing a form of seedlessness, viz. stenospermocarpy (SSC) from subgenus *Euvitis* Planch. into subgenus *Muscadinia* Planch. and the plants produced by the method. All publications cited in this application are herein incorporated by reference.

The goal of plant breeding is to combine in a single variety or hybrid various desirable traits. For fruiting crops, such as grapes (*Vitis*), these traits may include resistance to diseases and insects, tolerance to heat and cold, greater yield, better viticultural quality, high concentrations of antioxidant phytochemicals, ease of hand or mechanical harvesting of berries, uniform berry size and color, and pleasant aroma and flavor.

Grapes botanically belong to the family Vitaceae, which is divided into 16 genera. Of these, *Vitis* is the only genus with economic importance. The genus *Vitis* is divided into two subgenera, *Euvitis* Planch. and *Muscadinia* Planch. The subgenus *Euvitis* has 38 chromosomes and many berries borne in each cluster so that the general term 'bunch grape' is given to all species of *Euvitis*. *Muscadinia* has 40 chromosomes and smaller clusters, with a common name of muscadine grape.

More than 60 species have been described in *Euvitis*, including hundreds of known cultivars, which can be divided into three geographical groups: the American group, Asiatic group, and European and middle-Asian group. *Vitis vinifera* L. is a predominant commercial species grown all over the world, is the only member in the European and middle-Asian group, and has given rise to thousands of cultivars. The American group accounts for about 30 species, and a similar figure was estimated for the Asiatic group. Three species (*V. rotundifolia* Michx., *V. munsoniana* Simpson ex Munson, and *V. popenoei* Fennell) have been identified in the subgenus *Muscadinia*, *Vitis rotundifolia*, normally referred to as the muscadine grape, is the only species within *Muscadinia* with commercial value; however, hybridization with the two other species has broadened the genetic base for breeding improved forms of the muscadine.

The muscadine grape (*Vitis rotundifolia* Michx.) is native to the southeastern United States and was the first native grape species to be cultivated in North America. Wild muscadine grapes are functionally dioecious due to incomplete stamen formation in female vines and incomplete pistil formation in male vines. Male vines account for the majority of the wild muscadine grape population. Muscadine grapes are late in breaking bud in the spring and require 100-120 days to mature fruit. Typically, muscadine grapes in the wild bear dark fruit with usually 4 to 10 fruit per cluster. Bronze-fruited muscadine grapes (albino mutants) were likely found in the wild, propagated and grown in gardens as early as the early 1700's (Lawson, J. 1714. History of Carolina. W. Taylor and J. Baker, London). These eventually formed the basis of a fledgling wine industry, and in 1811, the name Scuppernong, a corruption of the native Algonquin Indian name for the locale of this industry, was applied to these bronze grapes. (Reimer, F. C. 1909. Scuppernong and other muscadine grapes: origin and importance. N. C. Agr. Expt. Sta. Bul. 201.) Bronze-fruited vines, probably mixtures of seedlings or genetic variants under the generic name Scuppernong formed the basis of a thriving wine industry from the late 1800's until Prohibition (Gohdes, C. 1982. Scuppernong, North Carolina's grape and its wines. Duke Univ., Durham, N.C.). Five distinct strains of grapes under the name Scuppernong have been identified (Woodroof, J. G. 1934. Five Strains of the Scuppernong Variety of Muscadine Grapes. Proc. Am. Soc. Hort. Sci. 32:384-385). There are over 100 improved cultivars of muscadine grapes that vary in size from ¼ to ½ inches in diameter and 4 to 15 grams in weight. Skin color ranges from light bronze to pink to purple to black. The flesh is clear and translucent for all muscadine grape berries with thick, tough skin and mucilaginous flesh; however, breeding efforts within *Muscadinia* have developed forms with superior textural qualities such as tender, crunchy skin and meaty/melting flesh. Muscadine berries are popular for making into wine, pies and jellies.

The morphological traits that further distinguish *Muscadinia* from *Euvitis* are that *Muscadinia* has unbranched tendrils, pith continuous through the node, conspicuous lenticels on the developing bark of current year shoots, and wood with a specific gravity greater than 1, meaning that it sinks in water.

*Vitis rotundifolia* is characterized by remarkable overall health, including high disease, insect, and nematode resistance. Muscadines have resistance to most *Euvitis* fungal diseases and Pierce's disease (PD), caused by the bacterium *Xylella fastidiosa* Wells, a limiting factor in the production of *V. vinifera* grapes in the southeastern United States. *Euvitis* species native to the southeastern United States have resistance or tolerance to most of these pests, and bunch grape hybrids with *V. vinifera* have been bred and have positive traits such as large cluster, edible skin and pulp and seedlessness, which have not been found in muscadine grapes. However, none of these *Euvitis* hybrids possess the strength of resistance and overall health of the muscadine. Hybridization of bunch grapes and muscadines to combine bunch grape fruit quality with superior health of *Muscadinia* has been a long-term goal for grape breeders.

The absence of seedlessness is the major obstacle for wide acceptance of muscadine grapes in the fresh fruit market. In contrast, seedlessness due to stenospermocarpy (SSC) has been well known in bunch grapes. SSC in grapes is characterized by abortion of ovule/seed development post syngamy and is distinguished from parthenocarpy, which is defined as the development of a seedless berry in the absence of syngamy. Nearly all of the commercially important seedless grape cultivars worldwide (primarily of the *Euvitis* species *Vitis vinifera* L.) exhibit SSC because parthenocarpic berries are unacceptably small by comparison. SSC likely occurred as a mutation in *V. vinifera* in Eurasia that was selected and perpetuated via asexual propagation since hardwood cuttings are easily rooted. There are no reports of a similar mutation in the domesticated *Muscadinia* species *V. rotundifolia* Michx., despite having been cultivated commercially for several hundred years over thousands of acres in its native habitat in the southeastern U.S.

Intersubgeneric crosses between muscadine and bunch grapes have been performed for more than a century by breeders in several grape breeding programs. *Vitis rotundifolia* will hybridize readily with some species of *Euvitis* when used as the male parent, but will rarely hybridize when used as the female parent. The failure to produce hybrids from the muscadine stigma pollinated with bunch grape pollen in various attempts over a century clearly indicates that a unilateral incompatibility exists between the *Muscadinia*×*Euvitis* crosses.

Therefore, it is desirable to combine the seedless characteristic of bunch grapes with the superior characteristics of the muscadine grape to develop a seedless muscadine grape variety.

The foregoing examples of the related art and limitations related therewith are intended to be illustrative and not exclusive. Other limitations of the related art will become apparent to those of skill in the art upon a reading of the specification.

SUMMARY OF THE INVENTION

In one aspect of the present invention, there is provided a method for introgressing stenospermocarpic seedlessness (SSC) from *Vitis* subgenus *Euvitis* Planch. across a partial sterility barrier and partial pollen incompatibility barrier into subgenus *Muscadinia* Planch. The major elements of the method may be summarized as comprising:

a. Crossing, using pollen of a SSC hermaphroditic plant of *Vitis vinifera* subgenus *Euvitis* Planch, or pollen of a SSC hermaphroditic *Euvitis* hybrid, with a sufficiently female fertile plant that is a hybrid of *Euvitis* and subgenus *Muscadinia* Planch to create from seeds thus obtained, plants that are a hermaphroditic SSC backcross to *Euvitis* and possess viable pollen that will be compatible with and fertilize female fertile plants of *Muscadinia* or of a largely *Muscadinia* hybrid;

b. Crossing, using pollen of said hermaphroditic SSC backcross to *Euvitis* plant, with a female fertile plant of *Muscadinia* or of a largely *Muscadinia* hybrid to create a so-called quasi-$F_1$ generation, from which are selected SSC quasi-$F_1$ segregants that may be further crossed with plants of *Muscadinia* or of a largely *Muscadinia* hybrid either 1) as a male, if said quasi-$F_1$ is hermaphroditic and has viable, compatible pollen, or 2) as a female, if embryos can be rescued in said further crosses;

c. Backcrossing, using either pollen or rescued embryos of said SSC quasi-$F_1$ segregants, to a plant of *Muscadinia* or of a largely *Muscadinia* hybrid to create a so-called quasi-$BC_1$ generation, from which are selected SSC quasi-$BC_1$ segregants that may be further crossed with plants of *Muscadinia* or of a largely *Muscadinia* hybrid either 1) as male, if said quasi-$BC_1$ is hermaphroditic and has viable, compatible pollen, or 2) as female, if embryos can be rescued in said further crosses; and d. Backcrossing, using either pollen or rescued embryos of said SSC quasi-$BC_1$ segregants, to a plant of *Muscadinia* or of a largely *Muscadinia* hybrid to create a so-called quasi-$BC_2$ generation, from which are selected SSC quasi-$BC_2$ segregant plants.

In another aspect of the present invention, there are provided plants of the genus *Vitis* containing the SSC trait in a *Muscadinia* background.

In another aspect of the present invention, there are provided plants of the genus *Vitis* containing the SSC trait in a *Muscadinia* background that are continuously fruiting.

In another aspect of the present invention, there are provided hermaphroditic SSC backcross to *Euvitis* plants and plant parts, including leaves, stems, roots, seeds, embryos, pollens, ovules, flowers, root tips, tissue, cells, fruit and the like.

In another aspect of the present invention, there are provided hermaphroditic SSC quasi-$F_1$ plants and plant parts, including leaves, stems, roots, seeds, embryos, pollens, ovules, flowers, root tips, tissue, cells, fruit and the like.

In another aspect of the present invention, there are provided hermaphroditic SSC quasi-$BC_1$ plants and plant parts, including leaves, stems, roots, seeds, embryos, pollens, ovules, flowers, root tips, tissue, cells, fruit and the like.

In another aspect of the present invention, there are provided hermaphroditic SSC quasi-$BC_2$ plants and plant parts, including leaves, stems, roots, seeds, embryos, pollens, ovules, flowers, root tips, tissue, cells, fruit and the like.

These and other aspects, as well as the scope, nature, and utilization of the claimed invention will be apparent to those skilled in the art from the following detailed description and appended claims.

DETAILED DESCRIPTION OF THE INVENTION

In the description and tables that follow, a number of terms are used. In order to provide a clear and consistent understanding of the specification and claims, including the scope to be given such terms, the following definitions are provided:

Allele. The allele is any of one or more alternative form of a gene, all of which relate to one trait or characteristic. In a diploid cell or organism, the two alleles of a given gene occupy corresponding loci on a pair of homologous chromosomes.

Backcrossing. Backcrossing is a process in which a breeder repeatedly crosses hybrid progeny back to one of the parents, for example, a first generation hybrid $F_1$ with one of the parental genotype of the $F_1$ hybrid. In the case of the present invention, the breeder would repeatedly cross hybrid progeny back to one of the parental subgenera, namely *Muscadinia*.

Calyptra. The corolla of the grape flower whose petals are fused at the distal end and which abscise at the proximal end, forming a cap which sheds at flowering.

Crossing. The pollination of a female flower of a grape plant, thereby resulting in the production of seed from the flower.

Cross-pollination. Fertilization by the union of two gametes from different plants.

Desired phenotypic traits. As used herein, refers to the desired phenotypic traits of a muscadine grape plant, including the recently developed traits of tender, crunchy skin and meaty/melting flesh. Desired phenotypic traits of muscadine also include the outstanding qualities of 1) superior resistance to a plethora of pests and diseases that make cultivation of *vinifera* difficult, expensive or impossible in the Southeast U.S., 2) superior ability to tolerate and resist freeze damage due to late frost, 3) superior concentrations of health promoting anti-oxidant phytochemicals in the fruit, 4) ability, in some cases, to allow mechanical harvesting of berries with dry stem scars, 5) distinctive, pleasant floral aroma and flavor and 6) naturally large and attractive berries.

Essentially all the physiological and morphological characteristics. A plant having essentially all the physiological and morphological characteristics means a plant having the physiological and morphological characteristics, except for the characteristics derived from the converted gene.

Extended-bearing. Normally, grapevines produce 2 or 3 inflorescences/clusters per primary shoot from primary buds. The floral primordia that give rise to these inflorescences are formed in developing primary buds in the season prior to their emergence. Some non-intersubgeneric genotypes produce 2 and rarely 3 inflorescences/clusters per lateral shoot in the current season. This is often referred to as a secondary crop that lags slightly behind the primary crop in ripening. Intersubgeneric hybrid vines that have an everflowering trait (EF), on primary and lateral shoots, continually produce inflorescences in the current season instead of tendrils, which are grasping structures thought to be evolutionarily derived from inflorescences. Consequently, there is a continuous succession of inflorescence production, flowering, fruit set, development and ripening along a shoot as long as it continues to grow. The season of bearing is thus extended. Hybrid genotypes vary in the extent to which inflorescences continue to be formed instead of tendrils. In the extreme case, inflorescences are produced to the exclusion of tendrils until the very end of the growing season when frost occurs.

Female fertile. Female fertile plants produce viable seeds or at least culturable embryos, and can include hermaphrodite plants.

Hermaphrodite. An organism having both functional male and female reproductive organs. Some grapevines have morphologically developed male (i.e. long upright stamens) and female (i.e. ovaries, styles and pistils) reproductive organs and may be considered genetically hermaphrodite; however, due to hybrid infertility caused by meiotic irregularities, can exhibit partial or total non-functionality of male and/or female gametes.

Muscadine. Botanically know as *Vitis rotundifolia*, muscadine is a grapevine species native to the Southeastern United States. Muscadine grapes have a number of outstanding qualities, including 1) superior resistance to a plethora of pests and diseases that make cultivation of *vinifera* difficult, expensive or impossible in the Southeast U.S., 2) superior ability to tolerate and resist freeze damage due to late frost, 3) superior concentrations of health promoting anti-oxidant phytochemicals in the fruit, 4) ability, in some cases, to allow mechanical harvesting of berries with dry stem scars, 5) distinctive, pleasant floral aroma and flavor and 6) naturally large and attractive berries. Muscadine grapes are typically consumed fresh and are used to make wine, juice and jelly. As used herein, 'largely *Muscadinia* hybrid' refers to plants that have a pedigree of at least 57.1% *Muscadinia*.

Parthenocarpy. The natural or artificially induced production of fruit without fertilization of ovules. Parthenocarpic fruit is therefore seedless. As used herein, parthenocarpy in interspecific muscadine hybrid ovules is indicated by bodies of less than 1.4 mm in length with translucent white coloration.

Plant cell. Plant cell, as used herein includes plant cells whether isolated, in tissue culture, or incorporated in a plant or plant part.

Plant habit. This is a visual assessment assigned during the late vegetative to early reproductive stages to characterize the plants leaf habit. It ranges from decumbent with leaves growing horizontally from the stalk to a very upright leaf habit, with leaves growing near vertically from the stalk.

Plant height. This is a measure of the height of the hybrid from the ground to the tip of the tassel, and is measured in centimeters.

Plant part. As used herein, the term "plant part" includes leaves, stems, roots, seeds, grains, embryos, pollens, ovules, flowers, ears, cobs, husks, stalks, root tips, anthers, silk, tissue, cells and the like.

Quantitative Trait Loci (QTL) Quantitative trait loci refer to genetic loci that control to some degree numerically representable traits that are usually continuously distributed.

Quasi-$BC_1$. As used herein, quasi-backcross 1 or quasi-$BC_1$ or q-$BC_1$ refers to a plant that is a backcross hybrid of *Euvitis* and *Muscadinia* created in a cross of *Muscadinia*×(*Muscadinia*×((*Euvitis*×*Muscadinia*)×SSC *Euvitis*)). Quasi-$BC_1$s are created in step c. of the present invention. The *Muscadinia* used in creation of q-$BC_1$ plants also include 'largely *Muscadinia* hybrids'.

Quasi-$BC_2$. As used herein, quasi-backcross 2 or quasi-$BC_2$ or q-$BC_2$ refers to a plant that is a backcross hybrid of *Euvitis* and *Muscadinia* created in a cross of *Muscadinia*×(*Muscadinia*×(*Muscadinia*×((*Euvitis*×*Muscadinia*)×SSC *Euvitis*))). Quasi-$BC_2$s are created in step d. of the present invention. The *Muscadinia* used in creation of q-$BC_2$ plants also include 'largely *Muscadinia* hybrids'.

Quasi-$BC_3$. As used herein, quasi-backcross 3 or quasi-$BC_3$ or q-$BC_3$ refers to a plant that is a backcross hybrid of *Euvitis* and *Muscadinia* created in a cross of *Muscadinia*×(*Muscadinia*×(*Muscadinia*×((*Euvitis*×*Muscadinia*)×SSC *Euvitis*)))). The *Muscadinia* used in creation of q-$BC_3$ plants also include 'largely *Muscadinia* hybrids'.

Quasi-$F_1$. As used herein, quasi-$F_1$ or q-$F_1$ refers to a plant that is a hybrid of *Euvitis* and *Muscadinia* created in a cross of *Muscadinia*×((*Euvitis*×*Muscadinia*)×SSC *Euvitis*). Quasi-$F_1$s are created in step b. of the method of the present invention. The *Muscadinia* used in creation of q-$F_1$ plants also include 'largely *Muscadinia* hybrids'.

Regeneration. Regeneration refers to the development of a plant from tissue culture.

Single gene converted. Single gene converted or conversion plant refers to plants which are developed by a plant breeding technique called backcrossing wherein essentially all of the desired morphological and physiological characteristics of an inbred are recovered in addition to the single gene transferred into the inbred via the backcrossing technique or via genetic engineering.

Stenospermocarpy (SSC). A heritable trait that induces cessation in development of ovules into potential seeds, even though fertilization has taken place. Variable timing of this cessation results in recognizable but limited development of seed structures, including the seed coat and endosperm, although the embryo may or may not continue to develop. The remains of the undeveloped seed can be seen in the fruit, which continues to develop and ripen. As used herein, 1.58 mm in length is the cut off for the smallest aborted seed trace with opaque pigmentation (green, red or brown), and any such trace with a greater measure than 1.58 mm in length is an example of stenospermocarpy. Not all of the typically 4 ovules per flower need to be fertilized to form a stenospermocarpic fruit, and usually, unfertilized and undeveloped ovules can be found along with seed traces in such fruits. Stenospermic vines can produce some seedless, parthenocarpic fruits, which are smaller than stenospermocarpic fruits, but none of the ovules ever show evidence of fertilization and remain small, translucent and white in color.

Transgene. A genetic sequence which has been introduced into the nuclear or chloroplast genome of a corn plant by a genetic transformation technique.

Variety. A plant variety as used by one skilled in the art of plant breeding means a plant grouping within a single botanical taxon of the lowest known rank which can be defined by the expression of the characteristics resulting from a given genotype or combination of phenotypes, distinguished from any other plant grouping by the expression of at least one of the said characteristics and considered as a unit with regard to its suitability for being propagated unchanged (International convention for the protection of new varieties of plants)

According to the invention, there is provided a method for introgressing a form of seedlessness, viz. stenospermocarpy (SSC) from subgenus *Euvitis* Planch. across a partial sterility barrier and partial pollen incompatibility barrier into subgenus *Muscadinia* Planch. and the plants produced by the method. Although breeders since 1859 recognized the potential in hybridizing *Euvitis* with *Muscadinia* (Loomis, N. H. 1963. A Bibliographical History of the Hybridization of *V. rotundifolia* and *Euvitis* Grapes. Unpublished Manuscript. 10 p), it was not until about 1980 that the idea of creating a seedless muscadine surfaced. Many were skeptical, because even with SSC, the typical muscadine, with its thick, tough skin and mucilaginous flesh, would still suffer from a competitive textural disadvantage with seedless *vinifera*. However, breeding efforts within *Muscadinia* have developed forms with superior textural qualities such as tender, crunchy skin and meaty/melting flesh. If SSC could be combined with these traits, then an overall textural package could be assembled that would permit consumption of the entire berry and thus offer competition to established seedless *vinifera* grapes. Add to this the muscadine's: 1) superior resistance to a plethora of pests and diseases that make cultivation of *vinifera* difficult, expensive or impossible in the Southeast U.S., 2) superior ability to tolerate and resist freeze damage due to late frost, 3) superior concentrations of health promoting anti-oxidant phytochemicals in the fruit, 4) ability, in some cases, to allow mechanical harvesting of berries with dry stem scars, and 5) distinctive, pleasant floral aroma and flavor, and it is not difficult to imagine the potential commercial impact of hybrid cultivars combining all of these traits.

The history of hybridizing *Euvitis* and *Muscadinia* up until 1992 was summarized by Goldy (Goldy, R. G. 1992. Breeding Muscadine Grapes. Horticultural Reviews 14:357-405). The earliest scientific investigations initiated separately in 1911 by Dearing (Dearing, C. 1917. Muscadine Grape Breeding. J. Hered. 8:409-424) and by Detjen (Detjen, L. R. 1919a. The limits in hybridization of *Vitis rotundifolia* with related species and genera. N.C. Agr. Expt. Sta. Tech. Bul. 17, Detjen, L. R. 1919b. Some $F_1$ hybrids of *Vitis rotundifolia* with related species and genera. N.C. Agr. Expt. Sta. Tech. Bul. 18) in North Carolina produced true $F_1$ hybrids between seeded forms of *V. vinifera* and *V. rotundifolia*, notably NCB4-50 and NC6-15 respectively, but a high degree of infertility led to the abandonment of these projects. Amateur and professional breeders continued to work with these $F_1$ hybrids. Fertile backcrosses to muscadine initially resulting from open pollinated seed of NCB4-50 were obtained in the 1940's and 1950's in a cooperative effort by Loomis, Farrer and Fry (Fry, B. O. 1964. Fertile interspecific hybrids *Vitis rotundifolia*×*Vitis vinifera*. Ga. Agr. Expt. Sta. Mimeo. Series N. S. 200). This line culminated in the release of several muscadine backcross cultivars. Southern Home (U.S. Plant Patent 9454), released in 1994, shows little or no evidence of the fruit characteristics of *V. vinifera*, from which it is six generations removed and it is mainly cultivated by amateurs for its ornamental cutleaf foliage. The cultivar Fry Seedless (U.S. Plant Patent 7296), released in 1988, exhibits an erratic production of small seedless parthenocarpic berries (Ramming, D. W., R. L. Emershad and R. Tarailo. 2000. A stenospermocarpic, seedless *Vitis vinifera*×*Vitis rotundifolia* hybrid developed by embryo rescue. HortScience 35:732-734) and is thought to be a highly infertile non-SSC hybrid that will very rarely set normally seeded berries. Dunstan obtained a notable fertile *Euvitis* backcross, DRX 55, by applying mixed *Euvitis* pollens to flowers of NC6-15 in 1954 (Dunstan, R. T. 1962. Some fertile hybrids of bunch and muscadine grapes. J. Hered. 53:299-303 (Corrigendum, 1963. 54:25)).

Systematic efforts in the 1950's and 1960's with newer $F_1$ hybrids at UC Davis by Jelenkovic and Olmo (Jelenkovic, G., and H. P. Olmo. 1968. Cytogenetics of *Vitis* III. Partially fertile $F_1$ diploid hybrids between *V. vinifera*×*V. rotundifolia* Michx. *Vitis* 7:281-293; Jelenkovic, G., and H. P. Olmo. 1969. Cytogenetics of *Vitis* IV. Backcross derivatives of *V. vinifera*×*V. rotundifolia* Michx. *Vitis* 8:1-11), further demonstrated that it was indeed possible to obtain true fertile backcrosses to *Euvitis*, some of which were quite productive and could produce acceptable vinifera-like wines (Olmo, H. P. 1971. *Vinifera rotundifolia* hybrids as wine grapes. Am. J. Enol. Vitic. 22:87-91). However, to date, no fruiting hybrid cultivars have been released. When evaluated in the Southeast U.S., the advanced *Euvitis* backcrosses lacked the overall complex disease resistance and adaptability of the muscadine. Although the muscadine resistance to many pests and diseases that afflict vinifera in the Southeast are genetically dominant, they were found to segregate independently in the backcrosses to *Euvitis* for the most part, and the probability of obtaining a backcross to *Euvitis* with the full complement of muscadine resistances is very low. Thus, while considerable excitement was generated by these breakthroughs, no practical or commercial import has been realized so far. Efforts are still underway in California and Europe to transfer resistances to specific pests and diseases from *Muscadinia* to vinifera (Merdinoglu D., S. Wiedeman-Merdinoglu, P. Coste, V. Dumas, S. Haetty, G. Butterlin, C. Greif. 2002. Genetic Analysis of Downy Mildew Resistance derived from *Muscadinia rotundifolia*. ISHS Acta Horticulturae 603: VIII International Symposium on Grape Genetics and Breeding; Ramming, D. W., F. Gabler, J. L. Smilanick, D A. Margosan, M. Cadle-Davidson, P. Barba, S. Mahanil, O. Frenkel, M. G. Milgroom, and L. Cadle-Davidson. 2012. Identification of Race-Specific Resistance in North American *Vitis* spp. Limiting *Erysiphe necator* Hyphal Growth. Phytopathology 102:83-93; Riaz, S., A. C. Tenscher, D. W. Ramming, and M. A. Walker. 2011. Using a limited mapping strategy to identify major QTLs for resistance to grapevine powdery mildew (*Erysiphe necator*) and their use in marker-assisted breeding. Theor. Appl. Genet. 122:1059-1073). Muscadine breeding programs, all of which have been conducted in the Southeast U.S., continue to pursue the elusive goal of transferring *vinifera* fruit quality characteristics to the muscadine, but the issues of infertility and incompatibility have forced most programs to focus their primary efforts on improving pure muscadines.

The accumulated experiences up to the late 1960's allowed several important generalizations regarding conventional hybridization of the subgenera at the diploid level, including pollen compatibility and fertility.

The $F_1$ cross between *Euvitis* (*V. vinifera*) and *Muscadinia* (*V. rotundifolia*) can be made with some difficulty, but much more readily when *Euvitis* is the female parent (E×M) (Jelenkovic, G., and H. P. Olmo. 1968. Cytogenetics of *Vitis* III. Partially fertile $F_1$ diploid hybrids between *V. vinifera*×*V. rotundifolia* Michx. *Vitis* 7:281-293; Patel, G. I. and H. P. Olmo. 1955. Cytogenetics of *Vitis*: I. The hybrid *V. vinifera*× *V. rotundifolia*. Amer. J. Bot. 42:141-159). This has been termed a one-way incompatibility barrier in which *Muscadinia* flowers display a strong aversion to *Euvitis* pollen. There are exceptions, but these are extremely rare. Though Patel and Olmo found that few pollen tubes of *V. vinifera* penetrated the styles of *V. rotundifolia* flowers and reached the ovule, they theorized that fertilization did not take place because no enlargement in the ovary was noted and flowers abscised at the same time as non-pollinated flowers (Patel, G. I. and H. P. Olmo. 1955. Cytogenetics of *Vitis*: I. The hybrid *V. vinifera×V. rotundifolia*. Amer. J. Bot. 42:141-159). More recently, Lu and Lamikanra (Lu, J. and O. Lamikanra. 1996. Barriers to intersubgeneric crosses between *Muscadinia* and *Euvitis*. HortScience 31:269-271) demonstrated that *Euvitis* pollen tube growth is largely arrested in the style near the stigma end of *Muscadinia* flowers. Jelenkovic and Olmo (Jelenkovic, G., and H. P. Olmo. 1969. Cytogenetics of *Vitis* IV. Backcross derivatives of *V. vinifera×V. rotundifolia* Michx. *Vitis* 8:1-11) found that this same incompatibility existed when *V. rotundifolia* flowers were pollinated by one male $F_1$, b54-17, (which evidenced some slight degree of pollen viability in staining and germination tests) and by four first-generation backcrosses to *Euvitis* ($BC_1E$) as absolutely no set of berries and seed occurred on 487 flowers/14 inflorescences and 1197 flowers/30 inflorescences, respectively. This unilateral pollen incompatibility has important implications in conventional attempts to transfer SSC from *Euvitis* to *Muscadinia* since the SSC *Euvitis* donor must enter as the male/pollen parent, itself possessing no female/seed functionality.

The $F_1$ hybrids generally display a very low level of fertility. Fertility varies between $F_1$s and this can be attributed to differences in *Euvitis* parentage. Jelenkovic and Olmo (Jelenkovic, G., and H. P. Olmo. 1968. Cytogenetics of *Vitis* III. Partially fertile $F_1$ diploid hybrids between *V. vinifera×V. rotundifolia* Michx. *Vitis* 7:281-293) posited that greater success with recently bred *vinifera* female parents could be due to their lower load of deleterious recessive genes compared to the higher load probably present in old line *vinifera* cultivars which were initially used with little success in hybridization (Patel, G. I. and H. P. Olmo. 1955. Cytogenetics of *Vitis*: I. The hybrid *V. vinifera×V. rotundifolia*. Amer. J. Bot. 42:141-159). The extreme example has been observed in derived hybrids with the perfect flowered morphology in which female fertility approaches normal, yet pollen of the very same plants with upright stamens is completely shriveled and non-functional. An additional phenomenon noted by Jelenkovic and Olmo is that fertility is often greater in flowers produced later in the season on lateral or secondary shoots.

When the tissue culture technique of embryo rescue was first applied to seedless grape breeding in the 1980's (Cain, D. W., R. L. Emershad, and R. E. Tarailo. 1983. In-ovulo embryo culture and seedling development of seeded and seedless grapes (*Vitis vinifera* L.). *Vitis* 22:9-14; Emershad, R. L. and D. W. Ramming. 1984. In-ovulo embryo culture of *Vitis vinifera* L. C. V. 'Thompson Seedless'. Am. J. Bot. 71:873-877; Spiegel-Roy, P., N. Sahar, J. Baron, U. Levi. 1985. In vitro culture and plant formation from grape cultivars with abortive ovules and seeds. J. Am. Soc. Hort. Sci. 110:109-112), it was viewed as a means of overcoming the unidirectional M×E pollen incompatibility because seedless *Euvitis* vines could newly be utilized as female parents and muscadines as pollinators, thus potentially facilitating the transfer of SSC from vinifera to muscadines. Ambitious projects were initiated by Goldy et al at NC State University (Goldy, R., R. Emershad, D. Ramming, and J. Chaparro. 1988. Embryo culture as a means of introgressing seedlessness from *Vitis vinifera* to *V. rotundifolia*. HortScience 23:886-889) and Lu et al at Florida A&M University (Lu, J., L. Schell and S. Lamikanra. 1993. Introgression of seedlessness from bunch grapes into muscadine grapes. Proc. Fla. State Hort. Soc. 106:122-124). Though both programs were able to produce a few $F_1$ hybrids that were SSC, neither was able to progress beyond that point due to problems with infertility. In a cooperative effort with Lu in 1995, berries of partially fertile JB SSC backcrosses to *Euvitis* that resulted from pollination by *Muscadinia* were sent by the Inventor to Florida A&M University for embryo rescue. Again, nothing resulted from this effort, possibly due to hybrid infertility. Ramming et al described a SSC $F_1$, C41-5, obtained cooperatively in work with Goldy, but no embryos were seen microscopically and none developed in embryo rescue (Ramming, D. W., R. L. Emershad and R. Tarailo. 2000. A stenospermocarpic, seedless *Vitis vinifera×Vitis rotundifolia* hybrid developed by embryo rescue. HortScience 35:732-734). Pollen germination of this $F_1$ hybrid reportedly ranged from 0 to 3% but Ramming communicated to the Inventor personally that it was not utilizable in breeding. Lu failed to obtain results in embryo rescue using C41-5 in crosses to muscadine pollinators and no berries resulted from selfing of 30 C41-5 inflorescences (Lu, J. 2001. The Grape Genetics, Breeding and Viticulture Program, Center for Viticultural Sciences, Florida A&M University. Report to SERA-IEG14 Group. 10 p). Grape breeding was terminated in about 1990 at NC State University which eventually discarded or lost all grapevine germplasm developed by public programs in North Carolina during the $20^{th}$ century.

In 1995, the Inventor began to have success in overcoming the pollen incompatibility exhibited by *Muscadinia* against seedless SSC pollinators, which theretofore had been pure *Euvitis*. Fertile SSC hybrid backcrosses to *Euvitis* ($BC_E$) were developed that had germinable pollen and, contrary to the results obtained by Jelenkovic and Olmo, a few from different backgrounds were discovered that could be used successfully to pollinate and fertilize pistillate muscadines. Two out of 24 tested SSC $BC_E$s, JB91-15-8-39 and JB92-51-2-51, in crosses to muscadines, were capable of fathering sizeable quasi-$F_1$ populations, and segregation of the population resulting from the former revealed that the SSC trait was more than likely conditioned by a single dominant gene in inter-subgeneric crosses.

Being intermediate in genetic constitution, these quasi-$F_1$s, like true $F_1$s, were expected to be only partially fertile. This was the case, again with male/pollen fertility seemingly more deleteriously affected than female/ovule fertility. By 2001, only one SSC quasi-$F_1$ had been identified whose pollen could be dried, extracted and still exhibit some germ tube formation in 20% sucrose, allowing it to be stored and used in further backcrosses to muscadines. It was found that muscadines themselves produce a far smaller proportion of pollen germ tubes in vitro in 20% sucrose than viniferas, so a more reliable indication of viability in muscadine-like vines may be the proportion of plump versus shriveled pollen grains and the formation of a bud-like structure that precedes germ tube formation in both muscadines and viniferas. Other SSC quasi-$F_1$s whose pollen did not form germ tubes after extraction would set scattered SSC fruit in open-pollination on late inflorescences when potential muscadine pollinators had already finished flowering. The Inventor surmised that some extremely low percentage of the fresh quasi-$F_1$ pollen must be viable and functional in selfing, regardless of the paucity of germ tubes in vitro. Accordingly, in 2002-3, fresh pollen of SSC quasi-$F_1$s started being used, a practice which likely enabled utilization of whatever low pollen fertility that exists in these intermediate quasi-$F_1$ hybrids, without the possible deleterious effects of several days of drying during the alternative extraction procedure. Such backcrossing to pure or largely muscadine pistillate vines has taken place for three generations and carried the SSC trait forward though each stage.

The present invention is distinguished from that of Goldy et al (Goldy, R., R. Emershad, D. Ramming, and J. Chaparro. 1988. Embryo culture as a means of introgressing seedlessness from *Vitis vinifera* to *V. rotundifolia*. HortScience 23:886-889) and Lu et al (Lu, J., L. Schell and S. Lamikanra. 1993. Introgression of seedlessness from bunch grapes into muscadine grapes. Proc. Fla. State Hort. Soc. 106:122-124) by the circumvention of the partial barrier of pollen incompatibility without resorting to the elaborate procedure of embryo rescue. Further, Goldy and Lu were laboring at the true $F_1$ generation with a much lower probability of fertility, especially male fertility, which is what is absolutely required to transmit SSC conventionally. They also were able to produce only a few hybrids, which greatly lowers the probability of isolating $F_1$ hybrids with fertility. The quasi-$F_1$ hybrids, NC74C049-10 and DRX 60-40 produced by Nesbitt and Dunstan (Dunstan, R. T. 1964. Hybridization of *Euvitis*×*Vitis rotundifolia*: backcrosses to muscadine. Proc. Am. Soc. Hort. Sci. 84:238-242), respectively, demonstrated that a better, more ovule fertile intermediate platform for breeding could be created by performing a reverse backcross to *Muscadinia*.

The current invention built upon the work of Nesbitt and Dunstan and demonstrated that pollen fertility could also possibly be enhanced in yet further reverse backcrosses to *Muscadinia*, thereby enabling the transfer of SSC from *Euvitis* to *Muscadinia* in a conventional manner. By virtue of the present invention, the SSC trait now exists in a *Muscadinia* context in combination with a number of important traits: 1) normal fertility allowing commercial production, 2) improved skin texture with desirable crunchiness and tenderness, allowing edibility, 3) improved flesh texture of a meaty/melting character that, together with SSC and improved skin texture, allows total edibility of the berry, 4) typical desirable muscadine aroma and flavor, 5) dry scar at the point of attachment of the berry to the pedicel, potentially allowing mechanical harvesting of grapes not only for processing purposes, but also for fresh fruit sold as loose berries with extended storage capability, 6) attractive red fall coloration of foliage, whereas all pure muscadines turn yellow, thus enhancing ornamental value, and 7) an everflowering trait, where inflorescences are produced continuously along the shoot instead of tendrils, resulting in an extended-bearing habit that could find utility in home garden or pick-your-own settings.

EXAMPLES

The present invention provides a method for introgressing SSC from *Euvitis* into *Muscadinia* and the plants produced by said method, demonstrated by the following Examples.

Example 1. Method for Introgressing a Form of Seedlessness, Viz. Stenospermocarpy (SSC) from Subgenus *Euvitis* Planch, into Subgenus *Muscadinia* Planch The present invention provides a method for introgressing stenospermocarpic seedlessness (SSC) from *Vitis* subgenus *Euvitis* Planch. across a partial sterility barrier and partial pollen incompatibility barrier into subgenus *Muscadinia* Planch. The major elements of the method may be summarized as comprising:

a. Crossing, using pollen of a SSC hermaphroditic plant of *Vitis vinifera* subgenus *Euvitis* Planch, or pollen of a SSC hermaphroditic *Euvitis* hybrid, with a sufficiently female fertile plant that is a hybrid of *Euvitis* and subgenus *Muscadinia* Planch to create from seeds thus obtained, plants that are a hermaphroditic SSC backcross to *Euvitis* and possess viable pollen that will be compatible with and fertilize female fertile plants of *Muscadinia* or of a largely *Muscadinia* hybrid;

b. Crossing, using pollen of said hermaphroditic SSC backcross to *Euvitis* plant, with a female fertile plant of *Muscadinia* or of a largely *Muscadinia* hybrid to create a so-called quasi-$F_1$ generation, from which are selected SSC quasi-$F_1$ segregants that may be further crossed with plants of *Muscadinia* or of a largely *Muscadinia* hybrid either 1) as a male, if said quasi-$F_1$ is hermaphroditic and has viable, compatible pollen, or 2) as a female, if embryos can be rescued in said further crosses;

c. Backcrossing, using either pollen or rescued embryos of said SSC quasi-$F_1$ segregants, to a plant of *Muscadinia* or of a largely *Muscadinia* hybrid to create a so-called quasi-$BC_1$ generation, from which are selected SSC quasi-$BC_1$ segregants that may be further crossed with plants of *Muscadinia* or of a largely *Muscadinia* hybrid either 1) as male, if said quasi-$BC_1$ is hermaphroditic and has viable, compatible pollen, or 2) as female, if embryos can be rescued in said further crosses; and d. Backcrossing, using either pollen or rescued embryos of said SSC quasi-$BC_1$ segregants, to a plant of *Muscadinia* or of a largely *Muscadinia* hybrid to create a so-called quasi-$BC_2$ generation, from which are selected SSC quasi-$BC_2$ segregant plants.

In another example of the method of the present invention, the female fertile plant that is a hybrid of *Euvitis* and subgenus *Muscadinia* Planch used in the crossing in step a. is any *Euvitis*×*Muscadinia* hybrid that produces seed.

In another example of the method of the present invention, an additional backcrossing is made, using pollen of said SSC quasi-$BC_2$ segregants, to a plant of *Muscadinia* or of a largely *Muscadinia* hybrid to create a so-called quasi-$BC_3$ generation, from which are selected SSC quasi-$BC_3$ segregant plants.

In a further example of the method of the present invention, one or more backcrosses to *Euvitis* are made at any point between steps a. through d.

Example 2. Sources of SSC for Hybrid Breeding Lines

The initial steps of the method of the present invention comprise crossing, using pollen of a SSC hermaphroditic plant of *Vitis vinifera* subgenus *Euvitis* Planch or pollen of a SSC hermaphroditic *Euvitis* hybrid, with a sufficiently fertile, functionally female seeded plant that is a hybrid of *Euvitis* and subgenus *Muscadinia* Planch to create plants that are a hermaphroditic SSC backcross to *Euvitis*. This hybridity is thought to enhance the ability of a SSC pollinator to fertilize female muscadines, thus overcoming the well-documented incompatibility of muscadine pistils with pure *Euvitis* pollen; however, the exact mechanism is unknown and the compatibility could be due to the contributions of the *Muscadinia* ancestors, the particular *Euvitis* parents, some particular combination of the two, or random chance. The hybrid breeding lines of the present invention include two vinifera sources of stenospermocarpic seedlessness (SSC), Centennial and USDA Fresno A97-27, which gave rise to Golden Gate (JB91-15-8-39=JB81-107-11×

Centennial) and Hoo-Hah (JB92-51-2-51=DRX60-40×USDA A97-27), respectively. Both Golden Gate (GG) and Hoo-Hah (HH) are perfect-flowered and have partial pollen viability and, though they are largely vinifera-like in character and composition, have sufficient pollen compatibility to fertilize female muscadines (or other largely muscadine hybrid females) and transmit the SSC trait to offspring.

These two SSC sources (GG and HH), differ in other respects, including important positive vinifera traits other than SSC that are lacking in muscadines, such as large cluster size (greater rachis elongation and greater floret/berry count) and muscat aroma/flavor. They also impart other traits that are likely strictly related to genetically confused states of wide hybridity, such as parthenocarpy, everflowering tendency and varying degrees of gametic malfunction. Other traits primarily from vinifera such as skin cracking tendency and berry elongation are important and closely followed.

SSC is evaluated when the seedling first has near-ripe or ripe fruit, typically from August-November. Vines that display SSC have seed traces (imperfectly developed ovules) that range from 1.58 mm (2/32") up to 7.2 mm (9/32") in length and generally have an imperfectly developed inner integument lacking the sclerification found in normal seed coats. Seed traces also generally lack endosperm. Only the largest traces and/or those with slight sclerification are noticeable or objectionable during consumption. Maximum seed trace length is measured and notes are made if the trace is objectionably noticeable. In most cases, seed traces are not noticeable in a *Muscadinia* background. Vines with large seed traces can transmit SSC and resulting offspring can have small unnoticeable seed traces. The first fruiting generally occurs 2-5 years after the cross is made. Once a hermaphroditic SSC vine is selected, it can be used in the following year as a pollinator.

Example 3. Characteristics of SSC Variety Golden Gate (GG)

GG is a representative plant of the hermaphroditic SSC backcross to *Euvitis* produced in step a. of the method of the present invention. GG is also known as JB91-15-8-39 and is a q-$BC_2E$ whose pedigree is 14.1% muscadine. GG is a partially pollen fertile backcross to vinifera and produces fairly healthy vines with only slight downy mildew late and is resistant to Target Spot and shows no sign of powdery mildew. GG also has a number of important characteristics, including an extended-bearing trait, a pronounced muscat flavor, SSC seedlessness, and a small to moderate cluster size with full set.

Muscat flavor has been transmitted in crosses of GG to pure muscadines, indicating that this may be a simply inherited dominant trait. On the other hand, the characteristic muscadine aroma/flavor appears attenuated or absent in intermediate hybrids and backcrosses to *Euvitis*-type grapes. Muscadine aroma/flavor appears to be a complex mixture of at least six compounds with character impact (Baek, H. H., K. R. Kadwallader, E. Marroquin and J. L. Silva. 2006. Identification of Predominant Aroma Compounds in Muscadine Grape Juice. J. Food Science. 62: 249-252). True muscadine aroma/flavor with full intensity is usually only regained after several generations of backcrossing to pure or largely muscadine parents.

The term, stenospermocarpy was coined by A. B. Stout (Stout, A. B. 1936. Seedlessness in Grapes. New York State Agric. Expt. Sta. (Geneva) Tech. Bull. 238), who found that SSC from Sultanina (aka Thompson Seedless) and Black Monukka was transmitted as a simple dominant trait in interspecific crosses with North American *Euvitis* hybrid clones derived primarily from *V. vinifera* and *V. labrusca*. SSC in GG is derived from Sultanina by way of Centennial, and in crosses of GG to pure muscadine females or largely muscadine hybrids, the SSC trait also appears to be conditioned by a single dominant gene, with about a 1:1 ratio of SSC:seeded offspring vines. Of 73 fruiting quasi-$F_1$ hybrids produced, 35 were SSC and 36 were seeded. Other researchers have found a variable and overall much lower proportion of SSC vines in crosses between seeded vines and SSC pollinators, mostly within vinifera. Some have even postulated that SSC is recessive in nature (Loomis, N. H. and J. H. Weinberger. 1979. Inheritance studies of seedlessness in grapes. J. Am. Soc. Hort. Sci. 104:181-184). As crosses are usually made in the field following emasculation, and thus subject to accidental selfing and/or contamination, it is possible that this could at least partly explain the lower proportion of seedless progeny in many straight vinifera crosses. While there are undoubtedly some modifying genetic factors which can influence the proportion of SSC vines in crosses within straight *Euvitis*, quasi-$F_1$ crosses between the largely *Euvitis* GG and pure muscadines are inter-subgeneric and true crosses are very easily recognized by several morphological markers. Thus, SSC is most likely conditioned by a single dominant gene in a muscadine context.

GG plants also have small to moderate cluster size with full set, far smaller than most table type vinifera, but larger than the largest muscadine. GG will transmit larger cluster size in backcrosses to muscadines, but the largest are not dramatically larger than the largest muscadines.

Example 4. Characteristics of SSC Variety Hoo-Hah (HH)

HH is a representative plant of the hermaphroditic SSC backcross to *Euvitis* produced in step a. of the method of the present invention. HH is also known as JB92-51-2-51 and is a q-$BC_{1E}$ whose pedigree is 31.3% muscadine. HH arose from a cross of DRX 60-40×USDA A97-27; DRX 60-40 is a 62.5% muscadine quasi-$F_1$ hybrid produced by Dunstan (Dunstan, R. T. 1964. Hybridization of *Euvitis*×*Vitis rotundifolia*: backcrosses to muscadine. Proc. Am. Soc. Hort. Sci. 84:238-242), which is an ovule fertile and pollen sterile hermaphrodite vine with large vinifera-like clusters and a very unusual fruity musky flavor. Additionally, DRX 60-40 is unusually cold hardy with little damage down to −6.4° F.

HH is a partially ovule fertile and partially pollen fertile vinifera backcross with straggly vinifera-form clusters up to 8 inches long. HH does not have a strong tendency to flower on laterals. About half of berries on HH are parthenocarpic, and berries are susceptible to cracking and rotting before fully ripe. The HH vine is susceptible to downy mildew and Target Spot. HH leafs out early and is susceptible to spring frost damage. The foliage of HH turns red in autumn with no apparent signs of leaf rolling.

Unlike GG, transmission of SSC by HH deviates from a 1:1 ratio. Among all fruiting quasi-$F_1$s, 26 were seeded, 12 were SSC, but an additional significant component of 22 seedlings appeared strictly parthenocarpic. Therefore, 31.6% of all vines showing evidence of fertilization are SSC. HH appears to transmit a high parthenocarpic tendency, which becomes apparent with the frequent total hybrid infertility (non-functional embryo sacs) encountered in these hybrids, probably whether the vines are genetically seeded or SSC.

Additionally, HH has large inflorescences, characteristic of vinifera table grapes and a red fall coloration of foliage. Many vinifera and hybrid cultivars exhibit red fall coloration, especially wine-type teinturiers, which seem to over-express anthocyanin pigments that are found not only in the berry pulp (normally only in the skin) but also in fall foliage. Red pigmentation of foliage is one of the symptoms of Leaf Roll Disease (LRD), which is associated with the presence of a closterovirus with nine known strains (GLRaVs). Red coloration of foliage in SSC muscadine backcrosses is sometimes accompanied by the rolling under of the leaf margin seen in LRD; however, LRD is not thought to be transmissible through seed, but potentially spread by scale and mealybugs.

HH is a homozygous hermaphrodite, which means that when it is crossed to a female, all offspring are hermaphrodite, since hermaphrodite is dominant to female. Obtaining homozygous hermaphroditic SSC hybrid parents is an important breeding goal as it would eliminate females from segregating populations. Crossing muscadine-like heterozygous hermaphrodites to each other to achieve this goal is problematic, since muscadines (and presumably muscadine-like hybrids) are extremely sensitive to emasculation, which usually causes the florets to abort, and in the absence of aborting they produce seeds that are selfs. Intentional selfing usually leads to inbreeding depression characterized by weakness and abnormalities. A way around this is to use as female parents, ovule-fertile vines with hermaphrodite form and pollen sterility due to hybrid infertility, such as DRX 60-40. The pattern "ovule fertile/pollen sterile" is relatively common among hermaphrodite hybrids of intermediate genetic composition.

There are other considerations in breeding seedless muscadines that apply equally to offspring of either GG or HH. Most important is that SSC berries of most clones, because of the imperfect development of the ovule, tend to be quite small by fresh market commercial standards for both muscadines and seedless viniferas. A smaller berry size could be acceptable if texture, sugar/acid ratio, aroma and flavor were outstanding, and a case could certainly be made that smaller berries are a healthier alternative, having a higher surface area/volume ratio, and thereby providing more fiber and anti-oxidants in the skins and less sugar in the pulp per weight of fruit. If berry size is a consideration, it may be possible, as vinifera breeders have done over the years, to obtain SSC selections with berries that are naturally larger (greater than 13/16") without unacceptably large seed traces and without the need for the costly operations of girdling and/or GA hormone application.

Another structural consideration is the nature of attachment of the berry to the pedicel. In the case of fruit harvested as whole clusters of a certain minimum size, strongly attached berries that cleanly detach without pieces of weak pedicels are desired. In the case of fruit harvested mechanically or manually and marketed as individual berries, well-attached berries that will withstand light jarring/winds but will release with dry scars with sufficient force are desired, meaning that the interior of the berry is sealed from infection by fungi/bacteria, thereby preventing a sticky mess and greatly extending shelf life. Wild muscadine berries naturally form a corky abscission layer between the berry and the pedicel upon ripeness, when they fall to the forest floor as a sealed unit, exuding their perfume to attract potential disseminators. Hybridization with the closely related species *V. munsoniana* has led to the development of the industry standard Carlos that hangs on, even when ripe, yet will detach with a dry scar with slightly more force than the simple weight of the berry. Among existing cultivars, Tara and Summit are in the same league with Carlos, suggesting that obtaining heavier berries in the 1" diameter size range is possible. Among pure muscadine selections of the present invention, only JB97-23-80-42, JB06-1-0-2, and JB99-1-4-15 exhibit this so-called "dry scar" characteristic. In addition to the dry scar, the ability of the berry to hang on through and beyond the point of ripeness, which is a human-selected trait, is very important.

Berry elongation is an attractive feature well known in vinifera table grapes. Muscadine berries, by and large, are spherical in shape. Hybridization of *V. rotundifolia* with *V. munsoniana* has introduced variability, which allows for the selection of moderately elongated berries. The trait seems to be recessive. For instance, the muscadine cultivar Doreen (Higgins×Dixie) has berries that measure 14/16"×12/16", for a length to width ratio of 1.167. Both parents of Doreen have munsoniana in their backgrounds and Higgins is slightly elongated, measuring 15/16"×14/16". Muscadine genes for berry elongation may work in concert with vinifera genes for berry elongation. For instance, when JB94-38-7-44 (14/16"×14/16") was crossed to JB98-13-1-10 (10/16"×10/16"), the SSC selection JB05-22-3-27 resulted, which has a range of berry sizes and shapes related to the degree of development of the ovules. Parthenocarpic berries are small and spherical or oblate, while the largest SSC berries measure 12/16"×9/16", for a length to width ratio of 1.33. When JB05-22-3-27 is backcrossed to the muscadine Pride (18/16"×17/16"), a range of berry shapes from spherical to very elongated berries with a length to width ratio of as high as 1.5 is observed, and a few are ovate and attractively pointed at the stylar end.

Example 5. Creation of SSC Quasi-$F_1$ Plants

The SSC quasi-$F_1$ plants presented herein are representative plants of the hermaphroditic SSC quasi-$F_1$ segregant plants produced in step b. of the method of the present invention. The creation of the quasi-$F_1$ generation took place from 1995-1999 (using GG) and from 1999-2004 (using HH). As soon as SSC appeared to be transmitted in dominant fashion, the search began for hermaphroditic SSC q-$F_1$s with functional pollen. Since the genetic composition of these SSC q-$F_1$ vines is intermediate (theoretically, GG q-$F_1$s are 57% M and HH q-$F_1$s are 65% M), pollen fertility was expected to be low due to irregularities during meiosis, typical of the true $F_1$ generation as a whole. Only one q-$F_1$, JB95-27-1 among many tested exhibited significant germination and growth of pollen tubes in a 20% sucrose solution following extraction, drying and storage, and for this reason was the only q-$F_1$ utilized in backcrossing for several years (1999-2001). Since it was observed that many q-$F_1$s whose pollen did not germinate in vitro would set a considerable number of SSC berries late in the season when pure muscadine pollinators had finished flowering, it was surmised that they must be selfing by virtue of a very low but usable level of pollen fertility. Therefore, during the 2002 season fresh pollen of a wider range of q-$F_1$s was used, employing whole inflorescences at anthesis as pollen applicators. This process gave fair to good results and has been followed ever since.

Example 6. Characteristics of SSC q-$F_1$ Variety JB02-27-3-9

JB02-27-3-9 is a hermaphroditic SSC quasi-$F_1$ plant produced by crossing JB97-20-6-23 and HH, and thus its pedigree is 44.1% muscadine. JB02-27-3-9 can set full attractive vinifera-like clusters, and has flavor that is slightly musky, with a very light muscat aroma. JB02-27-3-9 has a high incidence of berry cracking when ripe. Foliage of JB02-27-3-9 turns brilliant red in autumn, and the plants are resistant to downy mildew and to Target Spot, to which the DRX 60 series are highly susceptible. JB02-27-3-9 is used as a parent for SSC, cluster size, berry elongation and fall color.

Example 7. Characteristics of SSC q-$F_1$ Variety JB98-13-1-10 (Kokomo)

JB98-13-1-10, also known as Kokomo, is a hermaphroditic SSC quasi-$F_1$ plant produced by crossing Farrer 31-4 and GG, and thus its pedigree is 53.9% muscadine. JB98-13-1-10 sets fruit poorly on primaries and well on secondaries with an everflowering tendency. Berries are sweet with very good flavor and aromatics suggestive of coconut and grapefruit, similar to DRX 60-40, to which JB98-13-1-10 is not closely related. An ancestor of JB98-13-1-10 is Hunt, which was once considered the best dark-fruiting muscadine variety with excellent quality and high sugar. Seed trace is slightly hardened and slightly astringent, but still acceptable for whole eating, and berries do not crack or rot. The original vine of JB98-13-1-10 was killed to the ground in winter '10-'11, which saw only a low of 16° F., and the damage more than likely occurred in late February when freezing temperatures returned following a week of temperatures in the 70's. Most $F_1$ types share this weakness.

Example 8. Characteristics of SSC q-$F_1$ Variety JB00-1-0-4

JB00-1-04 is a hermaphroditic SSC quasi-$F_1$ plant produced by crossing Early Fry and HH, and thus its pedigree is 65.6% muscadine. JB00-1-0-4 sets straggly clusters on primaries and secondaries, with moderate cluster elongation that transmits to muscadine. JB00-1-0-4 does not display red fall color. Seed trace is slightly hardened and slightly astringent, and the skin cracks when berries are ripe.

Example 9. Characteristics of q-$F_1$ Variety JB97-20-6-23

JB97-20-6-23 is a female seeded quasi-$F_1$ plant produced by crossing Ga. 9-11-2 and GG, and thus its pedigree is 57% muscadine. JB97-20-6-23 sets well when pollinated and has an everflowering tendency on laterals. Clusters are often larger than the top end of muscadine range. JB97-20-6-23 has a strong muscat flavor, demonstrating that full muscat flavor from vinifera may be transmissible to further muscadine backcrosses. Skin cracks when berries are ripe. Many offspring of JB97-20-6-23 are weak and unfruitful, but a very light muscat flavor has been noted in a backcross to pure muscadine as well as a cross to HH. Breeding plans are to continue to use the JB97-20-6-23 vine to determine if full muscat flavor can be inserted into some normal vigorous SSC backcrosses.

Example 10. Characteristics of q-$F_1$ Variety JB95-27-1

JB95-27-1 is a hermaphroditic SSC quasi-$F_1$ plant produced by crossing Ga. 18-5 and GG, and thus its pedigree is 57% muscadine. JB95-27-1 has an everflowering tendency on primary and lateral shoots and produces mixtures of parthenocarpic and SSC fruit with laterals setting more SSC fruit. JB95-27-1 is a very healthy vine that is resistant to Target Spot, and the fruit cracks when ripe following rainfall. JB95-27-1 is one of the few q-$F_1$ that has germinable pollen in vitro in 20% sucrose.

Example 11. Characteristics of q-$F_1$ Variety JB98-11-0-3

JB98-11-0-3 is a hermaphroditic SSC quasi-$F_1$ plant produced by crossing Higgins and GG, and thus its pedigree is 57% muscadine. JB98-11-0-3 has an everflowering tendency on primary and lateral shoots, with a tendency for fruit to shrivel and fall before ripening begins. The ripe fruit is good for whole eating and shows no fruit cracking.

Example 12. Characteristics of q-$F_1$ Variety JB97-37-7-13

JB97-37-7-13 is a hermaphroditic SSC quasi-$F_1$ plant produced by crossing Ga. 9-11-2 and GG, and thus its pedigree is 57% muscadine. JB97-37-7-13 is a weak vine with abnormal leaf development characterized by undersized leaves with necrotic spots which prematurely shed. JB97-37-7-13 sets well with up to 20 berries per cluster when flowers are present, which is not often.

Example 13. Creation of SSC Quasi-$BC_1$ Plants

The SSC quasi-$BC_1$ plants presented herein are representative plants of the hermaphroditic SSC quasi-$BC_1$ segregant plants produced in step c. of the method of the present invention. Data presented on the sex and seedlessness of these quasi-$BC_1$ plants comes from vines that flowered and were considered true crosses by virtue of markers that are still quite recognizable in the quasi-$BC_1$ generation. Working with pollen of low viability invites ambient competition with contaminating muscadine pollen of normal potency, so a considerable number of vines were straight muscadines and not true crosses. This problem is amplified when female muscadine parents are directly adjacent to hermaphroditic muscadines. Another large contingent of planted vines are probably aneuploids, which are weak, cold tender and never attain flowering. Then there are those vines that flower, but due to hybrid sterility, never set any fruits over several years. In the $BC_1$ generation, the attrition rate is very high from seed to the fruiting stage, when seedlessness can finally be evaluated.

Example 14. Characteristics of SSC q-$BC_1$ Variety JB05-22-3-27

JB05-22-3-27 is a hermaphroditic SSC quasi-$BC_1$ plant produced by crossing JB94-38-7-44 and JB98-13-1-10, and thus its pedigree is 72.3% muscadine. JB05-22-3-27 continuously produces inflorescences instead of tendrils throughout the season on all shoots and sets full berry clusters with a mixture of small parthenocarpic berries up to 5/16"×5/16" and stenospermic berries up to 12/16"×9/16". Berries of JB05-22-3-27 are of excellent quality for eating whole when fully ripe and dark red to purple. The berries resist cracking and rot after heavy rains, but late in the season scattered ripe rot is seen on overripe berries. Very ripe berries late in the season are attractive to bees which can easily puncture the thin tender skin, so unless protected, all ripe fruit should be regularly harvested.

Example 15. Characteristics of SSC q-BC$_1$ Variety JB04-46-0-27

JB04-46-0-27 is a hermaphroditic SSC quasi-BC$_1$ plant produced by crossing JB99-1-4-15 and JB98-13-1-10, and thus its pedigree is 77% muscadine. JB04-46-0-27 has a strong everflowering tendency, but primaries eventually revert to producing tendrils. Laterals continue to flower with everflowering tendency, so flowers are present all season. As the original vine has aged, set has increased along with maximum berry size (up to $^{13}/_{16}"\times^{13}/_{16}"$), but overall set and berry size are erratic. A girdled cane set better with berries up to $^{13.5}/_{16}"\times^{13}/_{16}"$ and some clusters above muscadine size range. JB04-46-0-27 produces berries that are good for eating whole and have a very slight floral aroma characterized as "muscadine lite." Berries of JB04-46-0-27 are notable for their ability to resist cracking, rots and shelling during and after heavy rainfall periods.

Example 16. Characteristics of SSC q-BC$_1$ Variety JB05-4-4-5

JB05-4-4-5 is a female SSC quasi-BC$_1$ plant produced by crossing Pride and JB98-13-1-10, and thus its pedigree is 77% muscadine. JB05-4-4-5 has erratic setting, with better set on the relatively few lateral inflorescences and occasional well-filled attractive clusters. Berries of JB05-4-4-5 have a mild pleasant flavor and texture acceptable for whole eating. A girdled cane had much better set and berries were up to $^{13}/_{16}"\times^{12}/_{16}"$. Calyptra shedding is variable for JB05-4-4-5.

Example 17. Characteristics of SSC q-BC$_1$ Variety JB05-5-5-11

JB05-5-5-11 is a hermaphroditic SSC quasi-BC$_1$ plant produced by crossing Pride and JB00-1-0-4, and thus its pedigree is 82.8% muscadine. JB05-5-5-11 sets poorly on primaries but laterals set well, forming a slightly elongated cluster. Girdling increases set on primaries with compact clusters and berries up to $^{12}/_{16}"\times^{12.5}/_{16}"$. JB05-5-5-11 produces good quality berries for eating whole as early as first week of September and berries have a sweet mild fruity non-muscadine flavor. Berry skin is splotchy and not very attractive and shows some skin cracking after rains.

Example 18. Characteristics of SSC q-BC$_1$ Variety JB06-4-2-23

JB06-4-2-23 is a hermaphroditic SSC quasi-BC$_1$ plant produced by crossing Pride and JB02-27-3-9, and thus its pedigree is 72.1% muscadine. JB06-4-2-23 sets well on primaries and laterals with most inflorescences harvested for pollen. JB06-4-2-23 has slightly elongated clusters and girdled berries $^{11}/_{16}"\times^{10}/_{16}"$. JB06-4-2-23 is the most fertile SSC vine out of JB02-27-3-9 and like it, displays red foliage in autumn. Additionally, the JB06-4-2-23 vine shows rolling under of the leaf margin, which along with red coloration is a symptom of Grapevine Leafroll Disease (LRD) and should be isolated from other vines until it can be assayed for the associated viruses in 2013. JB06-4-2-23 is best used as a parent.

Example 19. Characteristics of SSC q-BC$_1$ Variety JB06-21-0-16

JB06-21-0-16 is a hermaphroditic SSC quasi-BC$_1$ plant produced by crossing Ga. 9-11-2 and JB00-1-0-4, and thus its pedigree is 82.8% muscadine. Parent Ga. 9-11-2 is notable for its crunchy skin adherent to a meaty flesh. JB06-21-0-16 displays generally good set with slightly irregular berry size and produces a considerable amount of fruit on laterals. Berries of JB06-21-0-16 are of good quality for eating whole as early as first week of September; however, berries show considerable skin cracking after rains. A weeping vine habit and unidentified leaf spotting were observed in 2012. Flowers of JB06-21-0-16 do not shed calyptras and must be physically removed to use as pollinator.

Example 20. Characteristics of SSC q-BC$_1$ Variety JB06-21-5-25

JB06-21-5-25 is a hermaphroditic SSC quasi-BC$_1$ plant produced by crossing Ga. 9-11-2 and JB00-1-0-4, and thus its pedigree is 82.8% muscadine. JB06-21-5-25 has generally good set with slightly irregular berry size and produces a considerable amount of fruit on laterals. JB06-21-5-25 has a slightly elongated cluster with potentially greater berry count than muscadines and is also one of earliest ripening backcrosses. Berries of JB06-21-5-25 have an almost neutral flavor and also have a large trace that although soft and green is noticeable during consumption. JB06-21-5-25 produces a very healthy vine, although berries show extensive skin cracking after rains.

Example 21. Characteristics of SSC q-BC$_1$ Variety JB00-16-0-1

JB00-16-0-1 is a hermaphroditic SSC quasi-BC$_1$ plant produced by crossing Ga. 9-11-2 and JB95-27-1, and thus its pedigree is 78.5% muscadine. JB00-16-0-1 displays erratic cropping and poor set on primaries, with better set on lateral inflorescences, which are common. JB00-16-0-1 shows no cracking or rot. Pollen of JB00-16-0-1 was tried in crosses to muscadine with no success, and selfed inflorescences do not set fruit. JB00-16-0-1 could be used as a parent in Embryo Rescue without emasculation as the large trace size suggests a good chance of culturing developing embryos.

Example 22. Characteristics of SSC q-BC$_1$ Variety JB02-19-1-24

JB02-19-1-24 is a hermaphroditic SSC quasi-BC$_1$ plant produced by crossing Pride and JB95-27-1, and thus its pedigree is 78.5% muscadine. JB02-19-1-24 displays erratic cropping and poor set on primaries, with better set on lateral inflorescences, which are common. JB02-19-1-24 can set well on primaries at the far end of a long cordon, which suggests a hormonal gradient may play a role in fertility. Berries can shell off with dry scar when beyond ripe and minimal skin cracking and no rot noted. Pollen of JB02-19-1-24 was tried in crosses to muscadine with no success. JB02-19-1-24 could be used as a parent in Embryo Rescue without emasculation, as large seed trace size suggests a good chance of culturing developing embryos.

Example 23. Characteristics of SSC q-BC$_1$ Variety JB03-20-1-21

JB03-20-1-21 is a hermaphroditic SSC quasi-BC$_1$ plant produced by crossing JB94-38-7-44 and JB98-11-0-3, and thus its pedigree is 73.8% muscadine. JB03-20-1-21 produces a healthy vine and sets well-filled clusters, often with more berries than largest muscadine clusters. Berries of JB03-20-1-21 are uniform in size with a mild and sweet flavor, but not much muscadine aroma. Berries of JB03-20-1-21 do not crack but are susceptible to ripe rot.

Example 24. Characteristics of SSC q-$BC_1$ Variety JB04-27-5-24

JB04-27-5-24 is a female SSC quasi-$BC_1$ plant produced by crossing JB94-38-7-44 and JB96-37-7-13, and thus its pedigree is 73.8% muscadine. JB04-27-5-24 sets well when pollenizers are nearby or when hand pollinated. Berries of JB04-27-5-24 are good for whole eating with good texture and flavor. Cane girdling increases set and berry size to $15/16"\times15/16"$. Plants of JB04-27-5-24 display no cracking or rot; however, the vine exhibits what is apparently a genetic disorder similar to its father's consisting of middling vigor and necrotic leaf spotting. JB04-27-5-24 has leaves that are undersized and many drop prematurely, hence JB04-27-5-24 is difficult to propagate. Grafting JB04-27-5-24 to a muscadine rootstock may ameliorate the condition. Additionally, this vine may have no fertile ovules at all, and may exhibit stimulative parthenocarpy, as no selfed inflorescences set any berries. Berries would be considered large for a parthenocarpic vine.

Example 25. Creation of SSC Quasi-$BC_2$ Plants

The SSC quasi-BC2 plants presented herein are representative plants of the hermaphroditic SSC quasi-BC2 segregant plants produced in step d. of the method of the present invention. $BC_2$ is the earliest backcross generation in which offspring have a reasonable chance of displaying normal vigor, cold hardiness, productivity and all the desired phenotypic traits of muscadine, including the typical aroma and flavor.

Example 26. Characteristics of SSC q-$BC_2$ Variety JB06-5-1-16

JB06-5-1-16 is a female SSC quasi-$BC_2$ plant produced by crossing Pride and JB03-20-1-21, and thus its pedigree is 86.9% muscadine. JB06-5-1-16 is a healthy vine with variable crop due to occasional to extensive dry calyptra (dc) which prevents pollination. JB06-5-1-16 has uniform berry size and attractive clusters that are occasionally well-filled. Girdling increased cluster compactness and increased berry size to $1"\times15/16"$, and trace size to $2\frac{3}{32}"$. Berries of JB06-5-1-16 hang on when ripe and detach with a high percentage of dry scars and with no cracking and very little rot.

Example 27. Characteristics of SSC q-$BC_2$ Variety JB06-5-1-26

JB06-5-1-26 is a hermaphroditic SSC quasi-$BC_2$ plant produced by crossing Pride and JB03-20-1-21, and thus its pedigree is 86.9% muscadine. JB06-5-1-26 has erratic set on primaries and full set on secondaries, with uniform berry size. Girdling increased set and berry size to $13/16"\times13/16"$. Berries of JB06-5-1-26 are sweet with good muscadine flavor in mid-September; however, the skin was judged a little tough for whole eating. Berries sequentially shell with dry scar as they ripen, but there is no cracking and practically no rot. Selfed inflorescences of JB06-5-1-26 set well.

Example 28. Characteristics of SSC q-$BC_2$ Variety JB06-5-6-18

JB06-5-6-18 is a hermaphroditic SSC quasi-$BC_2$ plant produced by crossing Pride and JB03-20-1-21, and thus its pedigree is 86.9% muscadine. JB06-5-6-18 sets well on primaries and secondaries which are abundant and lead to significant uneven ripening. Girdling increased berry size to $13/16"\times12/16"$. JB06-5-6-18 has slightly uneven berry size and berries color unevenly within the cluster with the sun side purple and shade side red. Berries of JB06-5-6-18 never get very sweet or develop full muscadine flavor. Minimal cracking but significant rot has been noted and the pedicel is quite weak which usually detaches with berry. Weakness in pedicel development can lead to some shriveling and shelling of berries which drop with a piece of the pedicel.

Example 29. Characteristics of SSC q-$BC_2$ Variety JB06-23-1-4

JB06-23-1-4 is a hermaphroditic SSC quasi-$BC_2$ plant produced by crossing Ga. 9-11-2 and JB03-20-1-21, and thus its pedigree is 86.9% muscadine. JB06-23-1-4 sets well with significant secondary crop and uniform berry size. Girdling increases berry size to $13/16"\times12.5/16"$ and seed trace in girdled fruit measures up to $5/32"$ in length. Berries of JB06-23-1-4 are ripe in the latter half of September and have average to good muscadine flavor, with some slight astringency noted in the skin but the fruit is not bad for whole eating. Skin toughness and flesh meltingness may ameliorate with advancing ripeness. Fruit of JB06-23-1-4 hangs with no shelling, no cracking and no significant rot into October, and over-ripe fruit shells with dry scar.

Example 30. Characteristics of SSC q-$BC_2$ Variety JB06-33-4-5

JB06-33-4-5 is a hermaphroditic SSC quasi-$BC_2$ plant produced by crossing JB97-23-7P-16 and JB03-20-1-21, and thus its pedigree is 86.9% muscadine. JB06-33-4-5 has very erratic cropping. JB06-33-4-5 may be the best flavored SSC backcross with true full muscadine character and has flesh that is almost totally melting and was judged as good for whole eating. Seed trace is not noticeable in JB06-33-4-5. Girdling yielded berries up to $15/16"\times14/16"$.

Example 31. Characteristics of SSC q-$BC_2$ Variety JB06-43-6-21

JB06-43-6-21 is a hermaphroditic SSC quasi-$BC_2$ plant produced by crossing JB99-1-4-15 and JB03-20-1-21, and thus its pedigree is 86.9% muscadine. JB06-43-6-21 sets well and is attractive with small lenticels. Berries of JB06-43-6-21 have very good muscadine flavor and are quite juicy, and the skin is judged to be slightly tough but crunchy and fruit can be eaten whole. Berries are ripe mid-September registering 18.5° Brix and appear to resist cracking and rotting.

Example 32. Characteristics of SSC q-$BC_2$ Variety JB08-38-1-10

JB08-38-1-10 is a hermaphroditic SSC quasi-$BC_2$ plant produced by crossing JB97-23-7P-37 and JB03-20-1-21, and thus its pedigree is 86.9% muscadine. JB08-38-1-10 is prolific of inflorescences which set very well with uniform berry size. The true production potential of JB08-38-1-10 was not fully evaluated as many primary inflorescences were used in pollinations. Clusters with up to 24 berries have been seen and JB08-38-1-10 is among the earliest coloring and ripening of $BC_2$s, peaking the first two weeks of September with 17.5° Brix. Berries lack muscadine flavor and seed trace is not noticeable. There is no cracking or rots seen in JB08-38-1-10. The mother of JB08-38-1-10, JB97-23-7P-37, is noted for meaty texture and scant muscadine aroma/flavor.

Example 33. Characteristics of SSC q-$BC_2$ Variety JB09-12-4-9

JB09-12-4-9 is a hermaphroditic SSC quasi-$BC_2$ plant produced by crossing Pride and JB05-22-3-27, and thus its pedigree is 86.1% muscadine. JB09-12-4-9 has a good fruit set.

Example 34. Characteristics of SSC q-$BC_2$ Variety JB09-16-4-23

JB09-16-4-23 is a hermaphroditic SSC quasi-$BC_2$ plant produced by crossing Ga. 9-11-2 and JB05-22-3-27, and thus its pedigree is 86.1% muscadine. JB09-16-4-23 sets well and has berries with a very mild muscadine flavor that is almost neutral, and berries are acceptable for whole eating.

Example 35. Characteristics of SSC q-$BC_2$ Variety JB09-16-4-14

JB09-16-4-14 is a female quasi-$BC_2$ plant produced by crossing Ga. 9-11-2 and JB05-22-3-27, and thus its pedigree is 86.1% muscadine. JB09-16-4-14 may be a possible embryo rescue parent.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. For example, if the range 10-15 is disclosed, then 11, 12, 13, and 14 are also disclosed. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

What is claimed is:

1. A method for introgressing stenospermocarpic seedlessness from *Vitis* subgenus *Euvitis* into subgenus *Muscadinia*, said method comprising:
   (a) crossing, using pollen of a SSC hermaphroditic plant of *Vitis vinifera* subgenus *Euvitis* Planch, or pollen of a SSC hermaphroditic *Euvitis* hybrid, with a sufficiently female fertile plant that is a hybrid of *Euvitis* and subgenus *Muscadinia* Planch to create from seeds thus obtained, plants that are a hermaphroditic SSC backcross to *Euvitis* and possess viable pollen that will be compatible with and fertilize female fertile plants of *Muscadinia* or of a largely *Muscadinia* hybrid;
   (b) crossing, using pollen of said hermaphroditic SSC backcross to *Euvitis* plant, with a female fertile plant of *Muscadinia* or of a largely *Muscadinia* hybrid to create a so-called quasi-$F_1$ generation, from which are selected SSC quasi-$F_1$ segregants that may be further crossed with plants of *Muscadinia* or of a largely *Muscadinia* hybrid either 1) as a male, if said quasi-$F_1$ is hermaphroditic and has viable, compatible pollen, or 2) as a female, if embryos can be rescued in said further crosses; and
   (c) backcrossing, using pollen of said SSC quasi-$F_1$ segregants, to a plant of *Muscadinia* or of a largely *Muscadinia* hybrid to create a so-called quasi-$BC_1$ generation, from which are selected SSC quasi-$BC_1$ segregants that may be further crossed with plants of *Muscadinia* or of a largely *Muscadinia* hybrid either 1) as male, if said quasi-$BC_1$ is hermaphroditic and has viable, compatible pollen, or 2) as female, if embryos can be rescued in said further crosses.

2. The method of claim 1, wherein said method further comprises:
   (d) backcrossing, using pollen of said SSC quasi-$BC_1$ segregants, to a plant of *Muscadinia* or of a largely *Muscadinia* hybrid to create a so-called quasi-$BC_2$ generation, from which are selected SSC quasi-$BC_2$ segregant plants.

3. The method of claim 2, wherein said method further comprises:
   (e) backcrossing, using pollen of said SSC quasi-$BC_2$ segregants, to a plant of *Muscadinia* or of a largely *Muscadinia* hybrid to create a so-called quasi-$BC_3$ generation, from which are selected SSC quasi-$BC_3$ segregant plants.

4. A hermaphroditic SSC backcross to *Euvitis* plant produced by the method of claim 1.

5. A hermaphroditic SSC quasi-$F_1$ plant produced by the method of claim 1.

6. A hermaphroditic SSC quasi-$BC_1$ plant produced by the method of claim 1.

7. A hermaphroditic SSC quasi-$BC_2$ plant produced by the method of claim 2.

8. A hermaphroditic SSC quasi-$BC_3$ plant produced by the method of claim 3.

9. The method of claim 1, wherein said method comprises embryo rescue.

10. The method of claim 1, wherein said method comprises backcrosses to *Euvitis*.

11. A plant of the genus *Vitis* having a pedigree containing both *Euvitis* and *Muscadinia*, wherein said plant is stenospermorcarpic, hermaphroditic and has one or more desired phenotypic traits of a muscadine grape plant.

12. The plant of claim 11, wherein said plant is continuously fruiting.

13. A tissue culture produced from protoplasts or cells from the plant of claim 11, wherein said cells or protoplasts are produced from a plant part selected from the group consisting of leaf, pollen, ovule, embryo, cotyledon, hypocotyl, meristematic cell, root, root tip, pistil, anther, flower, berry, seed, shoot, stem, pod and petiole.

14. A grapevine plant regenerated from the tissue culture of claim 13.

15. A method of producing a commodity plant product, said method comprising obtaining the plant of claim 11, or a part thereof, and producing the commodity plant product from said plant or plant part thereof, wherein said commodity plant product is selected from the group consisting of whole grapes (fresh or frozen), raisins, fruit leather, paste, puree, freeze-dried fruits, nutraceutical preparations, wine, juice, jam and jelly.

* * * * *